(12) United States Patent
Takeuchi et al.

(10) Patent No.: US 11,638,895 B2
(45) Date of Patent: May 2, 2023

(54) GAS SENSOR AND METHOD FOR PRODUCING SAME

(71) Applicants: Figaro Engineering Inc., Minoo (JP); University Public Corporation Osaka, Osaka (JP)

(72) Inventors: Masato Takeuchi, Sakai (JP); Junpei Furuno, Sakai (JP); Tatsuya Tanihira, Minoo (JP); Kenichi Yoshioka, Minoo (JP)

(73) Assignees: Figaro Engineering Inc., Osaka (JP); University Public Corporation Osaka, Osaka (JP)

( * ) Notice: Subject to any disclaimer, the term of this patent is extended or adjusted under 35 U.S.C. 154(b) by 847 days.

(21) Appl. No.: 16/489,894

(22) PCT Filed: Feb. 19, 2018

(86) PCT No.: PCT/JP2018/005657
§ 371 (c)(1),
(2) Date: Aug. 29, 2019

(87) PCT Pub. No.: WO2018/159348
PCT Pub. Date: Sep. 7, 2018

(65) Prior Publication Data
US 2020/0001223 A1   Jan. 2, 2020

(30) Foreign Application Priority Data
Mar. 2, 2017 (JP) .............. JP2017-039572

(51) Int. Cl.
*B01D 53/02* (2006.01)
*G01N 27/12* (2006.01)

(52) U.S. Cl.
CPC ........... *B01D 53/02* (2013.01); *G01N 27/126* (2013.01); *B01D 2253/106* (2013.01);
(Continued)

(58) Field of Classification Search
CPC ...... B01D 2253/106; B01D 2253/1124; B01D 2253/20; B01D 2253/25; B01D 2257/556;
(Continued)

(56) References Cited

U.S. PATENT DOCUMENTS

2011/0052462 A1* 3/2011 Schmidt ............ B01D 53/8668
977/762
2016/0250618 A1* 9/2016 Long .................. B01J 31/1691
423/648.1
(Continued)

FOREIGN PATENT DOCUMENTS

| JP | 11262658 A | 3/1999 |
| JP | 2007112948 A | 5/2007 |

(Continued)

OTHER PUBLICATIONS

Translation of JPWO2017138190A1; Kita (Year: 2017).*
International Search Report for International Application No. PCT/JP2018/005657.

*Primary Examiner* — Christopher P Jones
(74) *Attorney, Agent, or Firm* — The Webb Law Firm

(57) ABSTRACT

The filter of a gas sensor comprises an inorganic porous support supporting both an organic sulfonic acid compound including sulfo group (—SO3H) and a Lewis acid having at least a metal element of transitional metal elements, Al element, Ga element, In element, Ge element, and Sn element. The Lewis acid loaded in the inorganic porous support adsorbs low concentration siloxanes. The organic sulfonic acid compound including sulfo group polymerizes adsorbed siloxanes in the filter so as not to desorb from the filter.

6 Claims, 13 Drawing Sheets

(52) U.S. Cl.
CPC .. *B01D 2253/1124* (2013.01); *B01D 2253/20* (2013.01); *B01D 2253/25* (2013.01); *B01D 2257/556* (2013.01); *B01D 2259/45* (2013.01)

(58) Field of Classification Search
CPC .. B01D 2259/45; B01D 53/02; G01N 27/126; G01N 27/16; G01N 27/4077; G01N 33/0009; G01N 33/0047; G01N 33/005
See application file for complete search history.

(56) References Cited

U.S. PATENT DOCUMENTS

2016/0279601 A1* 9/2016 Osswald ............ B01D 46/0036
2017/0182475 A1* 6/2017 Wendland ................ B01J 39/19

FOREIGN PATENT DOCUMENTS

| | | |
|---|---|---|
| JP | 2011212565 A | 10/2011 |
| JP | 20130088267 A | 11/2014 |
| JP | 2015044175 A | 3/2015 |
| JP | 2015100753 A | 6/2015 |
| JP | 2015230278 A | 12/2015 |
| WO | 2017138190 A1 | 8/2017 |

* cited by examiner

Fig. 4

| Specimen | Acid Content ($H^+$ mmol/g) | Specific Surface Area [$m^2/g$] |
|---|---|---|
| Amberlyst 15 | 4.67 | 38 |
| $SiO_2$ gel-$SO_3H$ | 0.24 | 293 |
| $SiO_2$ gel-COOH | 0.08 | 261 |
| $SO_3/ZrO_2$ | 0.26 | 93 |
| fumed $SiO_2$ (A300) | 0.05 | 289 |
| SBA-15-p | 0.05 | 782 |
| Zr-SBA-15-p | 0.10 | 865 |
| 5SA-Zr-SBA-15-p | 0.11 | 692 |
| 10SA-Zr-SBA-15-p | 0.38 | 731 |
| 20SA-Zr-SBA-15-p | 0.80 | 753 |
| 30SA-Zr-SBA-15-p | 0.99 | 696 |
| 10SA-SBA-15-p | 0.25 | 610 |

US 11,638,895 B2

GAS SENSOR AND METHOD FOR PRODUCING SAME

CROSS-REFERENCE TO RELATED APPLICATIONS

This application is the United States national phase of International Application No. PCT/JP2018/005657 filed Feb. 19, 2018, and claims priority to Japanese Patent Application No. 2017-039572 filed Mar. 2, 2017, the disclosures of which are hereby incorporated by reference in their entirety.

BACKGROUND OF THE INVENTION

FIELD OF THE INVENTION

The present invention relates to a gas sensor and a method for producing the same and, in particular, to the filter thereof.

DESCRIPTION OF RELATED ART

Gas sensors have a problem; they may be poisoned by trace amounts of siloxanes in the environment. Regarding the poisoning by siloxanes, one of the applicants has proposed a filter comprising a mixture of zeolite and active alumina (Patent Document 1: JP2013-88267A).

Patent Document 2 (JP2015-100753A) discloses a siloxane removal filter comprising a silica-gel supporting ferric sulfate (III) or zirconium sulfate. Patent Document 2 discloses that adsorbed siloxanes may desorb from the filter. In other words, the siloxane filters need not only the adsorption capacity for siloxanes but also the capacity for retaining the adsorbed siloxanes without desorbing.

PRIOR TECHNICAL DOCUMENTS

Patent Documents

Patent Document 1: JP2013-88267A
Patent Document 2: JP2015-100753A

SUMMARY OF THE INVENTION

The Problem to be Solved

The object of the invention is:
to provide a filter having a high absorption capacity for siloxanes and a retaining capacity for adsorbed siloxanes by polymerizing them in the filter to prevent the desorption, and a producing method of the filter; and
to enhance the durability of gas sensors to siloxanes.

Means for Solving the Problem

A gas sensor according to the invention comprises
a gas sensing element and a filter arranged at a position nearer to atmospheres to be detected than the gas sensing element;
wherein the filter comprises an inorganic porous support supporting both an organic sulfonic acid compound including sulfo group ($—SO_3H$) and a Lewis acid having at least a metal element of transitional metal elements, Al element, Ga element, In element, Ge element, and Sn element.

Inorganic porous supports when loaded in it the Lewis acid, such as a Zr oxide, become to adsorb siloxanes at low concentrations (FIG. 3). The mesoporous silica shown in FIG. 3 before loading Lewis acid and before loading sulfo group adsorbs only small amounts of siloxanes at low concentrations. The loading of Lewis acid makes the filter adsorb siloxanes present in environments at low concentrations.

Since the Lewis acid itself can not polymerize the adsorbed siloxanes to oligomers, the adsorbed siloxanes may move in the filter, desorb from the filter eventually, and contaminate gas sensing element. However, when an organic sulfonic acid compound having sulfo group is loaded in the inorganic porous support, siloxanes are polymerized and become not to desorb from the inorganic porous support (FIG. 5). Thus, siloxanes are fixed in the filter.

When loading, in the inorganic porous support, the Lewis acid and the organic sulfonic acid compound containing sulfo group, the resultant filter adsorbs siloxanes from low concentrations and does not allow the desorption. Gas sensors with this filter have high durability against siloxanes (FIGS. 8, 10, and 13).

The filter according to the invention may be prepared by loading a constitutional metal element of the Lewis acid in the inorganic porous support and then, loading the organic sulfonic acid compound in the inorganic porous support. The accurate relation between the metal element and the sulfo group in the filter prepared by this method is not clear; in particular, it is difficult to confirm to what extent the sulfo group and the fixed metal element are separated in their locations. The filter material according to the invention is obtainable, for example, by a step for loading, in the inorganic porous support, at least a salt of a metal element of transitional metal elements, Al element, Ga element, In element, Ge element, and Sn element, and then, thermally decomposing the salt to load the Lewis acid including an oxide of the metal element, and by a subsequent step for loading, in the inorganic porous support, the organic sulfonic acid compound including sulfo group ($—SO_3H$) to prepare the material of the filter.

The filter prepared by the method has a by far higher siloxane removal capacity than the filter prepared by loading a metal element and sulfonic acid as a metal sulfate (FIG. 13). Therefore, the essential is Lewis acid adsorbing siloxanes at low concentrations and the organic sulfonic acid compound polymerizing the adsorbed siloxanes to oligomers, not a metal sulfate. The metal element in the metal sulfate does not work as a Lewis acid and the sulfo group in the sulfate is weak as an acid due to the combination to the metal atom.

The Lewis acid includes preferably at least a metal element of transitional metal elements, Al element, Ga element, In element, Ge element, and Sn element; however, precious metal elements, Cd, Hg, and Tc are not preferable. More preferable metal elements are Zr which was used in the experiments, and at least a chemically analogous element of elements having atomic number from 21 to 32, Y, Nb, Mo, Hf, Ta, W, In, and Sn. These metal elements may be presumed as forming fine clusters in the support as oxides or the like, and at least a part of these elements exists as an oxide. From the preparation condition of the filter, these metal elements are presumed as existing mainly as an oxide; however, a part of them may be present as a salt with the organic sulfonic acid. These metal elements may substitute for the framework element in the inorganic porous support and so may form a solid solution with the inorganic porous support.

The organic sulfonic acid compound including sulfo group is, for example, p-toluene sulfonic acid. Organic sulfonic acid compounds adsorb more strongly to the inorganic porous support than sulfuric acid, less form salts with the metal element in the Lewis acid by moving in the filter, and less flows out of the filter when condensed. The organic sulfonic acid compound concentration is, in reduction to the concentration of S element making sulfo group, preferably down to 0.2 g and up to 4 g in 100 g inorganic porous support. The concentration of metal element making Lewis acid, such as Zr, is preferably down to 10 mmol and up to 200 mmol in 100 g inorganic porous support.

As already known, phenolic hydroxyl group binds strongly with inorganic porous support surface, such as silica-gel surface. When phenol sulfonic acid compounds are used in place of p-toluene sulfonic acid, the bonding between the inorganic porous support and the sulfonic acid compound is strengthened so that the reaction between the sulfonic acid compound and the metal element in the Lewis acid is further suppressed. Here, the OH group position in the phenol sulfonic acid compound may be any of o, m, and p.

For strengthening the bond between the organic sulfonic acid compound and the inorganic porous support, the support surface may be reformed by catechol ($\varphi$-(OH)2: $\varphi$ is a benzene ring.) or the like. Catechol adsorbs strongly on the support surface by two hydroxyl groups, and the organic sulfonic acid compound adsorbs on the catechol surface or the like by $\pi$ electron interaction, for example.

The organic sulfonic acid compound may be phenol sulfonic acid, catechol di-sulfonic acid, a bis-phenol compound introduced with sulfo group ((OH)(SO3H)$\varphi$-CH2-$\varphi$(SO3H)(OH) or the like), and naphthalene sulfonic acid. The number of sulfonic acid groups per molecule is at least one and arbitrary. These molecules may be condensed.

The inorganic porous support has preferably a large specific surface area, the capability of supporting the organic sulfonic acid compound and the Lewis acid, and a mean pore diameter for allowing the siloxane diffusion (down to 3 nm and up to 30 nm when calculated from the BET specific surface area and the pore volume gotten in the examination). For example, active charcoal, zeolite, silica-alumina, and so on may be usable.

Preferable inorganic porous supports are plate-like mesoporous silica, silica-gel other than mesoporous silica, and alumina. The inorganic porous support includes plate-like mesoporous silica, silica-gel other than mesoporous silica, or alumina, and more preferably, the inorganic porous support consists of at least one member of plate-like mesoporous silica, silica-gel other than mesoporous silica, and alumina. Particularly preferably, the inorganic porous support includes silica-gel other than mesoporous silica, and further preferably, the inorganic porous support consists of silica-gel other than mesoporous silica. With the silica-gel support, a filter easily preparable and having high siloxane removal capacity is resultant.

BRIEF DESCRIPTION OF THE DRAWINGS

[FIG. 4] A diagram indicating H+ acid contents and specific surface areas of the mesoporous silicas according to the embodiment and comparative examples.

DESCRIPTION OF THE INVENTION

The best embodiment and other embodiments will be described in the following embodiments.

Embodiment Using Plate-Like Mesoporous Silica

Figure 1:
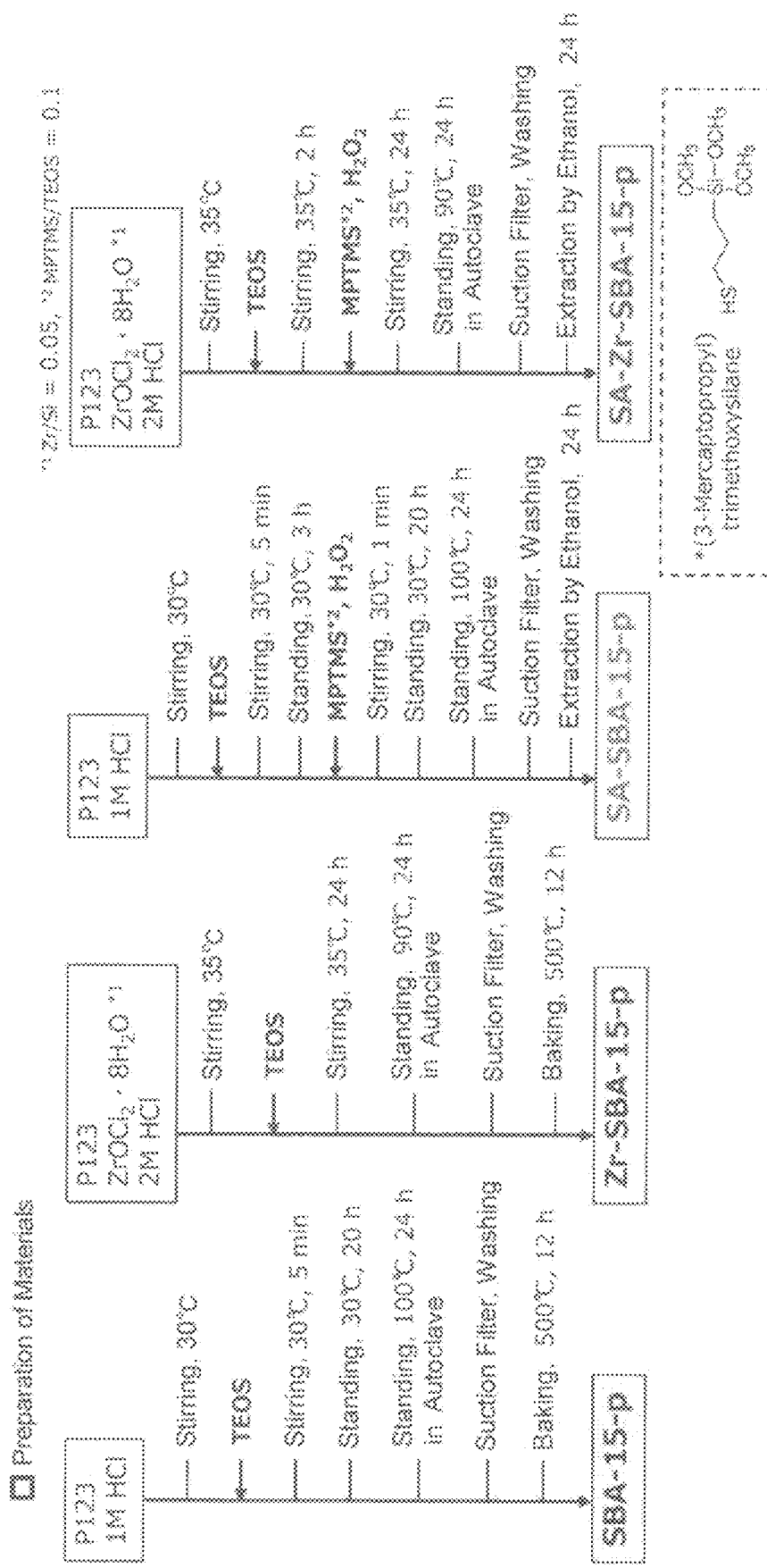
[FIG. 1] A diagram indicating the preparation condition of mesoporous silica according to an embodiment.
Figure 2:
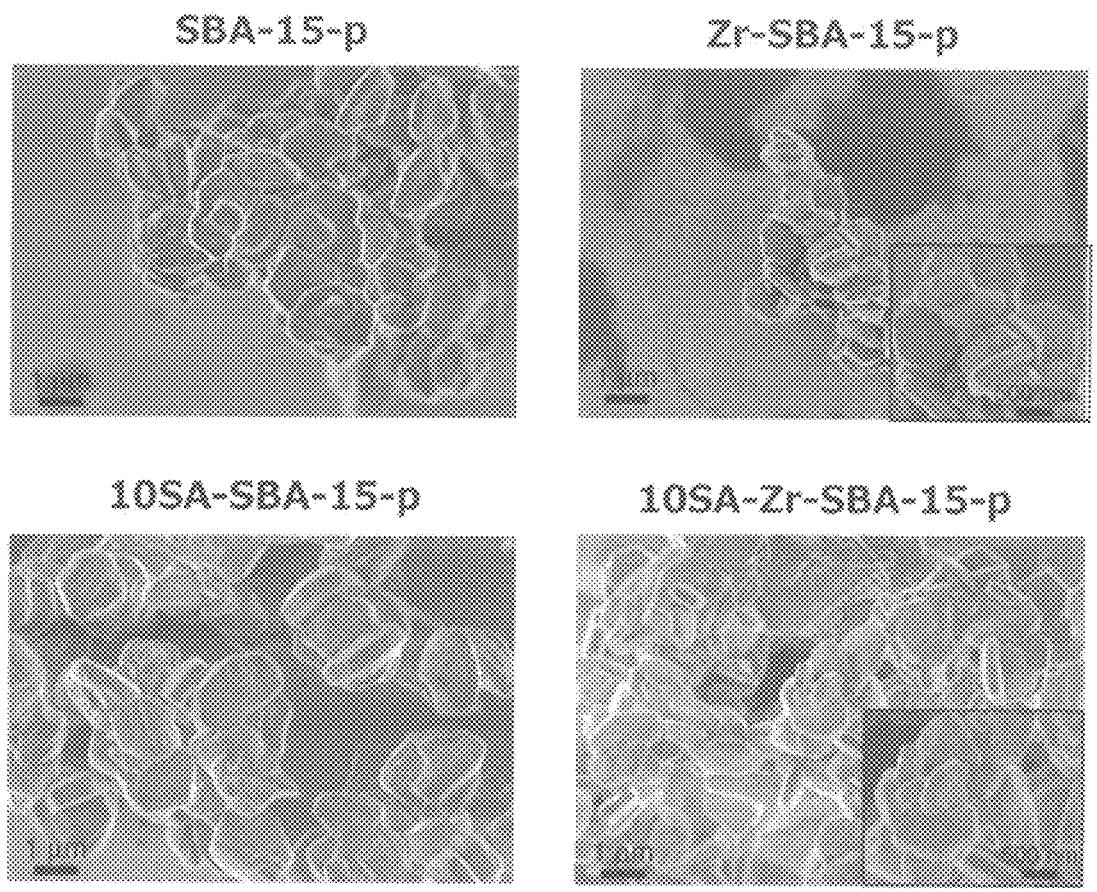
[FIG. 2] Electron microscopic images of the mesoporous silicas according to the embodiment and comparative examples.

FIGS. 1-12 indicate an embodiment using plate-like mesoporous silica. FIG. 1 indicates the preparation condition of the mesoporous silica according to the embodiment. In the drawing, P123 denotes Pluonic P123 Surfactant, TEOS denotes Tetra-Ethoxy-Ortho-Silicate, and MpTMS denotes 3-mercapto-propyl-trimethoxy-silane. SBA-15 indicates a species of prepared mesoporous silica, Zr indicates the inclusion of Zr element, SA indicates the inclusion of sulfo group, and p in SBA-15-p indicates a plate-like morphology of SBA-15 particles.

Usual mesoporous silica comprises rod-like particles and has mesopores along the longitudinal direction of the rods. In the embodiment, the preparation conditions were chosen to prepare plate-like SBA-15. To a 1M hydrogen chloride solution containing P123, a TEOS solution was mixed under stirring at 30° C., the mixture was stirred and then was made stand still. The mixture was treated in an autoclave at 100° C. for 24 hours. The product was suction filtered, washed with pure water, and then, baked at 500° C. for 12 hours to prepare plate-like SBA-15-p.

When Zr element was made an ingredient, the atomic ratio of Zr and Si at the charging stage was set, for example, to 1:20, and ZrO2 was added into the P123 solution to prepare Zr-SBA-15-p. Zr was present, in the framework of mesoporous silica, as a substituent for the Si atom; in other words, Zr was present in the framework of mesoporous silica as a solid solution. When Zr element is included, the atomic ratio of Zr/Si is, for example, 1:100-1:8. In place of Zr element, Ti element, Ta element, or Nb element may be included in the mesoporous silica, with a similar atomic ratio of these atoms and Si.

In SA-SBA-15-p, the mesoporous silica includes sulfo group. An organic silicon compound having S element was mixed and oxidized, for example, by hydrogen peroxide, to introduce sulfo group in the mesoporous silica. The introduction method of sulfo group is arbitrary; however, it is preferable to add the organic silicon compound including S element, before the growth of mesoporous silica in the autoclave. The oxidation of the S element to the sulfo group may be carried out at any time. In FIG. 1, the atomic ratio of S element and Si element at the charging stage was set to 1:11; however, the experiment was carried out in the range of 1:21-3:13. When Zr element was included, the atomic ratio of Zr and Si was 1:20 in FIG. 1; the preferable range is 1:100-1:10.

Figure 3:
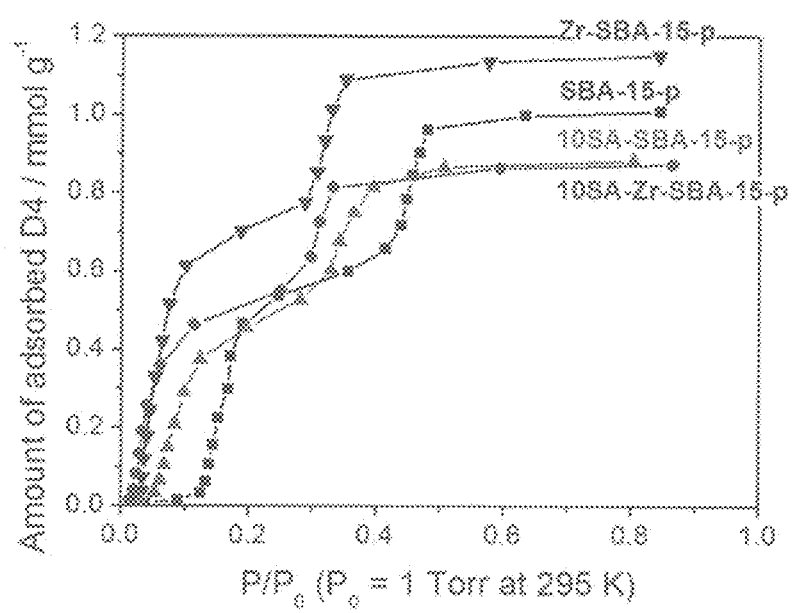
[FIG. 3] A diagram indicating the adsorption isotherms of a cyclic siloxane to the mesoporous silicas according to the embodiment and comparative examples.

For each specimen prepared, X-ray diffraction spectrum and adsorption and desorption isotherm were measured to confirm the presence of regular mesopores. FIG. 3 shows scanning electron microscopic images of the specimens in FIG. 1. The mesoporous silica particles are nearly hexagonal and plate-like. The depth directions of the mesopores are along the thickness direction of the plates, the thickness of the plates is about 200 to 300 nm, the diameters of the plates (the diagonal length of the hexagons) are about 1 µm, and the average aspect ratio of the diameter and the thickness is about 3:1 to 10:1. When loading Zr element, the particle size was observed to become smaller, and the morphology control to plate-like particles from rod-like particles became easier. Further, when loading sulfo group, the hexagonal shape was slightly disturbed. When loading Ti element, W element, Mo element, Nb element, or Ta element, in place of Zr element, the same tendency was observed.

FIG. 3 indicates adsorption isotherms of a cyclic siloxane (D4) on the specimens. The filters in gas sensors are required to remove siloxanes at very low concentrations, and the rise in the adsorption amount at the low concentration side is important. A specimen including Zr (▼) and a specimen including Zr and sulfo group (●) have large adsorption amounts of the siloxane at low concentrations. Further, a specimen including only sulfo group (▲) has a larger adsorption amount of the siloxane at low concentrations than a specimen not including sulfo group nor Zr (■). As FIG. 3 shows, it is effective for increasing the adsorption amounts of siloxanes at low concentrations to include Zr or both Zr and sulfo group in mesoporous silicas.

FIG. 4 indicates H+ acid contents and BET specific surface areas of the mesoporous silicas and other adsorbents. Here, the H+ acid contents were measured by the following method: 0.1 g of adsorbent was added into 20 mL of 2M NaCl aqueous solution and then was stirred under reduced pressure in order to exchange H+ in the adsorbent by Na+. Then, the mixture was filtered, and 10 mL of the filtered liquid was acid-base titrated for measuring H+ contents. The plate-like mesoporous silica was found to have a large specific surface area and its H+ content increased by the introduction of sulfo group or Zr element.

Figure 5:
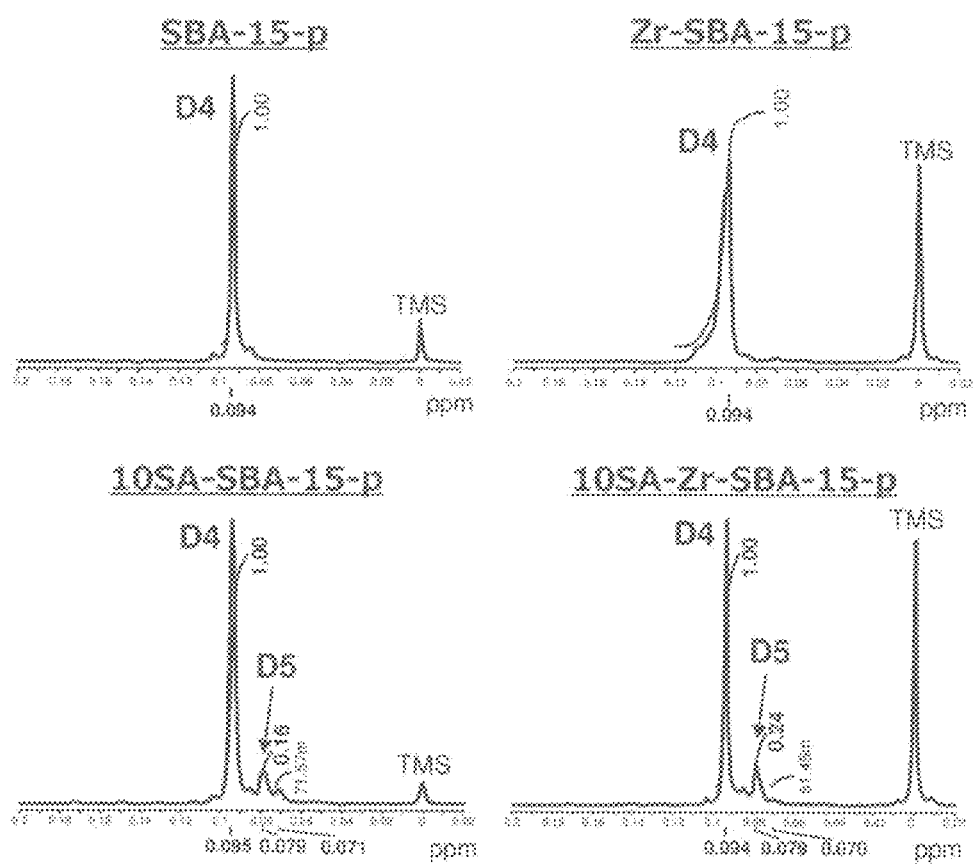
[FIG. 5] A diagram indicating 1H NMR spectra of the cyclic siloxanes adsorbed in the mesoporous silicas according to the embodiment and comparative examples.

FIG. 5 indicates 1H NMR spectra of cyclic siloxanes adsorbed in the mesoporous silicas. Each specimen was pretreated at 200-400° C. in vacuum and then was kept in an atmosphere containing D4 at the saturated pressure at room temperature for 1 hour. Then, siloxanes were extracted from 100 mg specimens to CDCl3, for measuring the 1HNMR. In the drawing, numerals such as "1.00" indicate relative peak areas, and TMS indicates a peak for Tetra-Methyl-Silane, the standard substance.

From the mesoporous silicas having sulfo group and having large H+ contents, a peak for a distinct siloxane, D5 was detected. This indicates the sulfo group carried out the ring-opening-polymerization of siloxanes and fixed siloxanes in the mesoporous silicas. In contrast to this, from a specimen containing only Zr, D5 was not detected. In addition, in a specimen including both the sulfo group and Zr, the generation amount of D5 was further increased. In view of these facts with the results in FIG. 3, we may conclude that Zr adsorbs siloxanes at low concentrations and that the sulfo group carries out the ring-opening-polymerization of the siloxanes.

Gas Sensor

Figure 6:
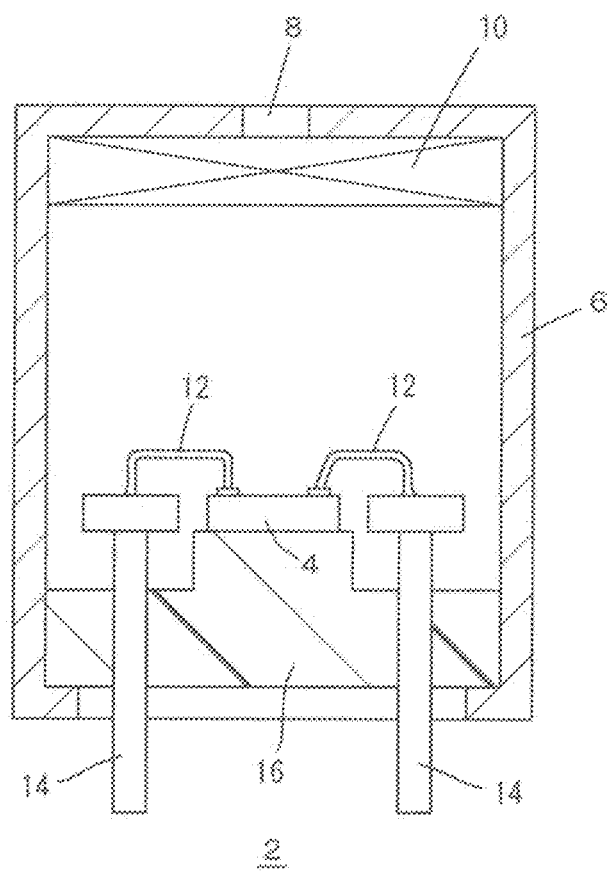
[FIG. 6] A cross-sectional view of a gas sensor according to the embodiment.

FIG. 6 indicates the structure of the gas sensor 2. The gas sensing element 4 in the gas sensor 2 has a mems structure and includes SnO2 as the gas sensing material. On a thin film of tantalum hemi-pentoxide over a cavity in a Si substrate, a Pt heater was formed and was covered by an interlayer insulating film, and a pair of electrodes and a SnO2 thick film were formed on the insulating film, to form the gas sensing element 4. The gas sensing element 4 was accommodated within a metal can 6 having an opening 8 at the top. From the opening, an atmosphere to be detected is provided through a mesoporous silica filter 10 to the gas sensing element 4. Indicated by 12 are leads, by 14 are pins, and by 16 is the base.

The structures and materials of the gas sensor are arbitrary except for the filter material. The gas sensing element may use other metal oxide semiconductors than SnO2, may be a Pt catalyst bead, or may be an electrochemical gas sensing element that uses an electrolyte. The filter is arbitrary except for the inorganic porous support supporting a Lewis acid and an organic sulfonic acid compound having sulfo group. For example, the above filter material may be mixed with another filter material, or the layer of another filter material and the layer of the above filter material are provided in the filter.

Figure 7:
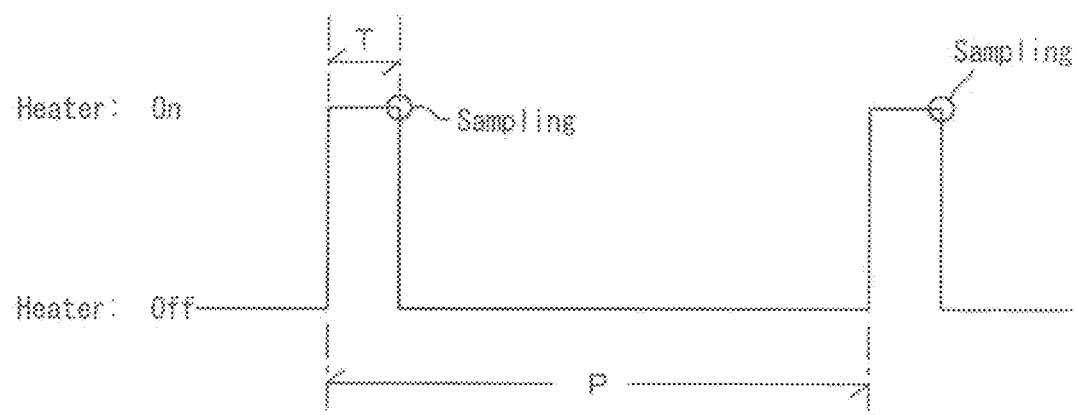
[FIG. 7] A diagram indicating the driving pattern of the gas sensor according to the embodiment.

FIG. 7 indicates the driving condition of the gas sensor. The gas sensor 2 is driven with a period P, the heater is made on for a time width T in each period, and the signal of the gas sensor 2 is sampled synchronously when the heater is made turned off. In consideration of reducing the heater power, the period P is set to 30 seconds and the time width T is set to 1 second, as the standard driving condition. When the detection delay tests to gases were performed, the period P was set to 1 second, and the time width T was set to 0.1 seconds. The temperature of SnO2 when the signal being sampled was made about 350° C. for the detection of isobutane (FIGS. 8, 9) and was made about 450° C. for the detection of methane (FIGS. 10-12).

Figure 8:
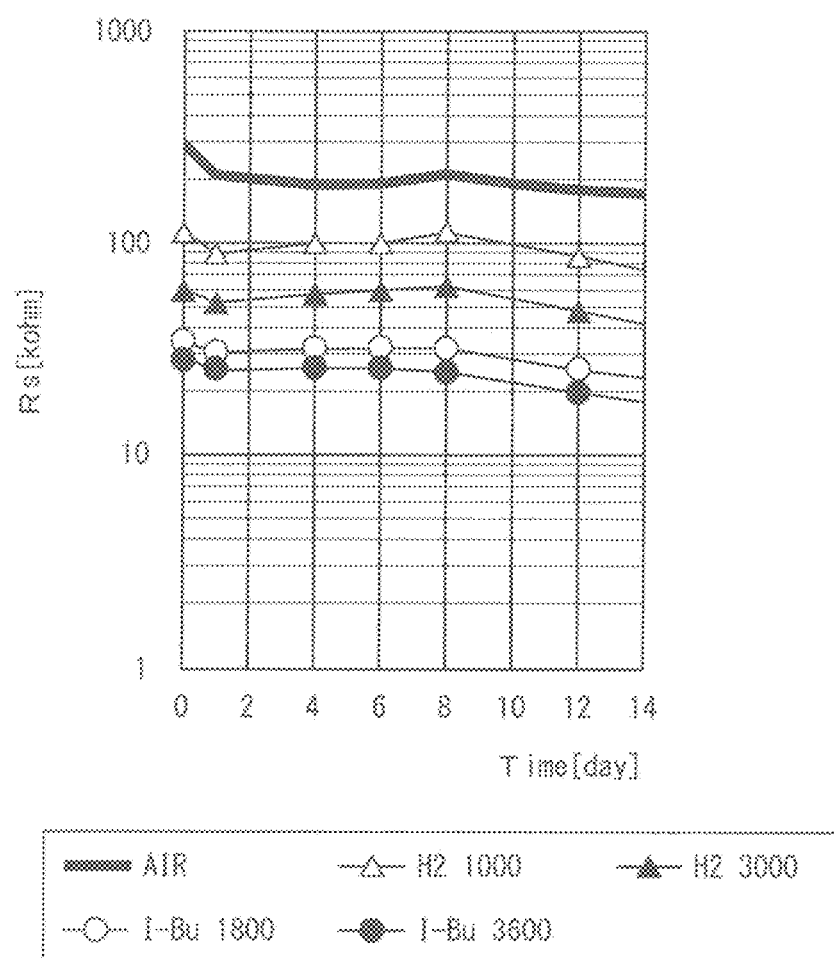
[FIG. 8] A diagram indicating behavior of resistance of the gas sensor in air, in hydrogen, and in isobutane, during a durability test to siloxanes according to the embodiment.
Figure 9:
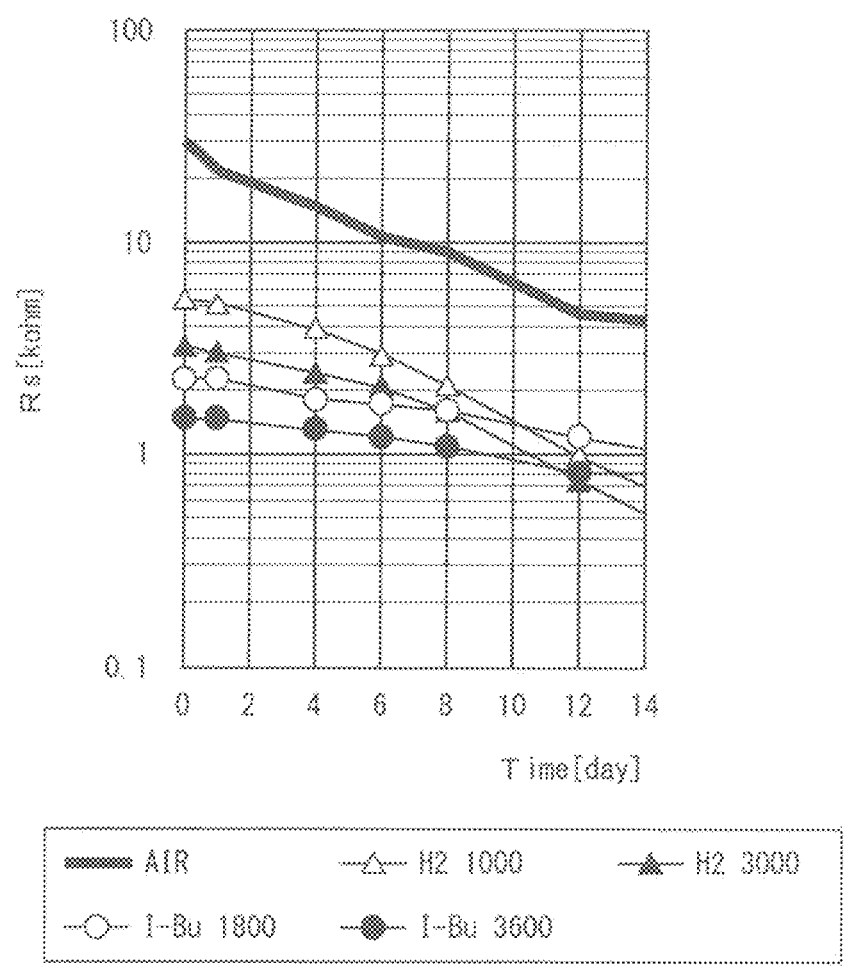
[FIG. 9] A diagram indicating behavior of resistance of a conventional gas sensor in air, in hydrogen, and in isobutane, during a durability test to siloxanes.

In an atmosphere containing siloxanes M3, D4, and D5, 10 ppm for each, the gas sensors 2 were driven for 12 days, and the resistances of the gas sensors 2 were measured intermittently in atmospheres comprising clean air and predetermined concentrations of gases. The results according to the embodiment (the filter contained 45 mg of 10SA-Zr-SBA-15-p) are shown in FIG. 8. The results according to a conventional filter using a mixture of zeolite and active alumina (the composition of silica: alumina was 1:1 by mass ratio and the amount was 60 mg) are shown in FIG. 9. The degree of poisoning in the embodiment was within an allowable range, but the degree of poisoning in the conventional example was out of the allowable range.

Figure 10:
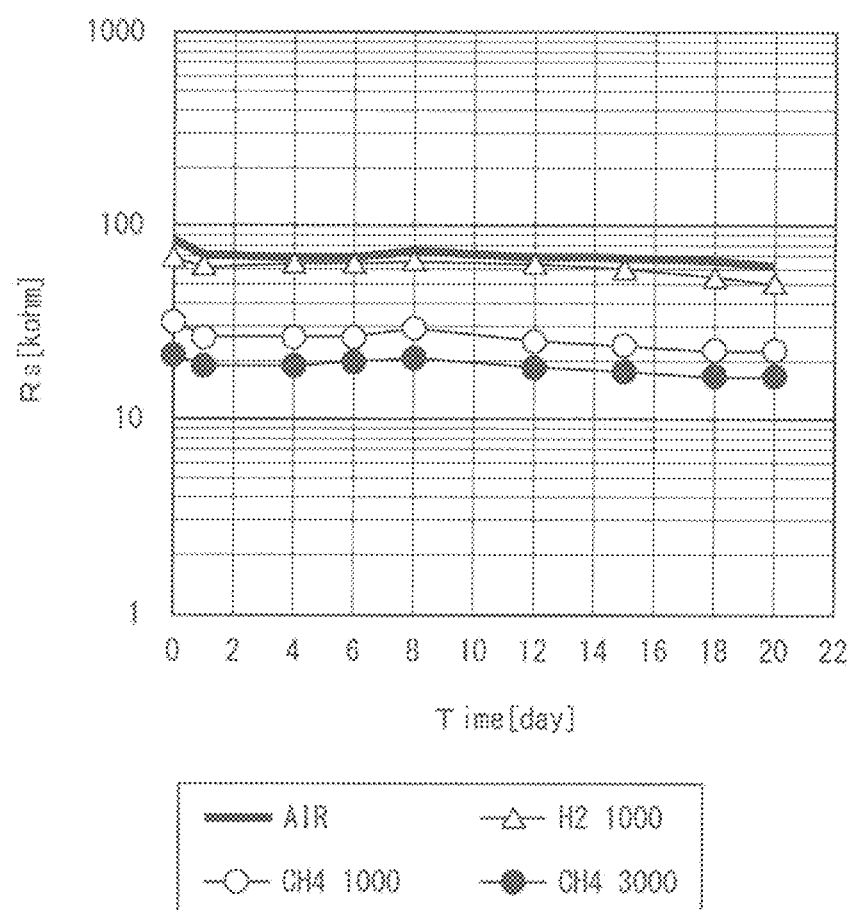
[FIG. 10] A diagram indicating behavior of resistance of a gas sensor according to the embodiment, with a mesoporous silica filter comprising plate-like particles and having sulfo group in air, in hydrogen, and in isobutane, during a durability test to siloxanes.
Figure 11:
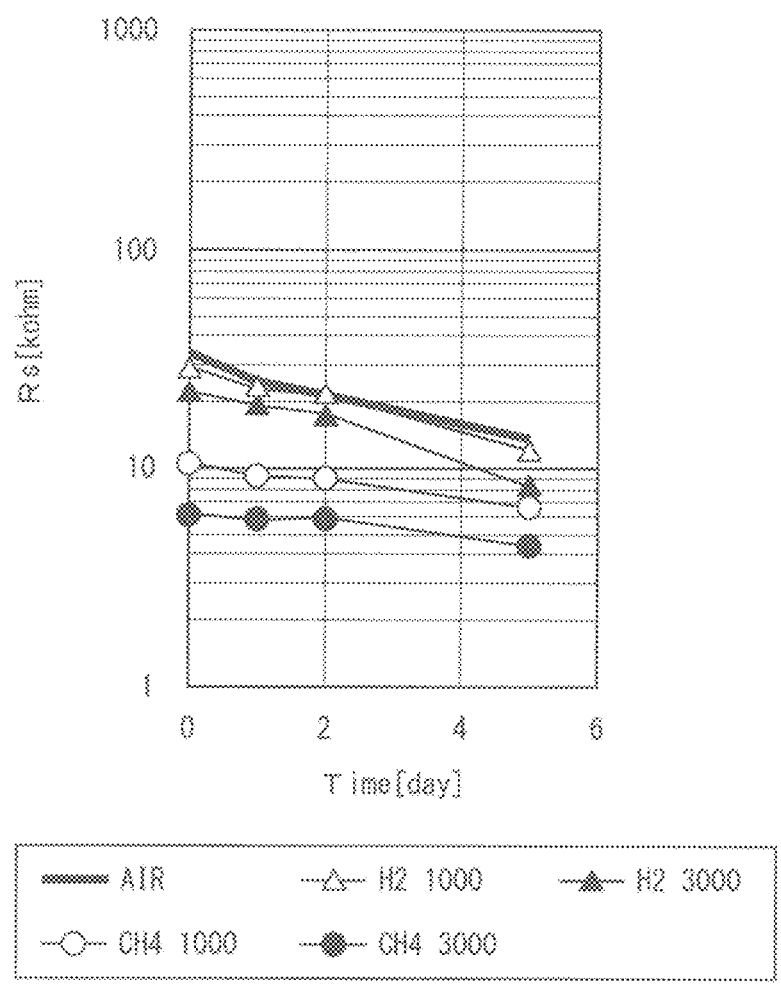
[FIG. 11] A diagram indicating behavior of resistance of a comparative gas sensor in air, in hydrogen, and in isobutane, during a durability test to siloxanes, with a mesoporous silica filter comprising plate-like particles but not including an organic sulfonic acid compound nor Lewis acid.
Figure 12:
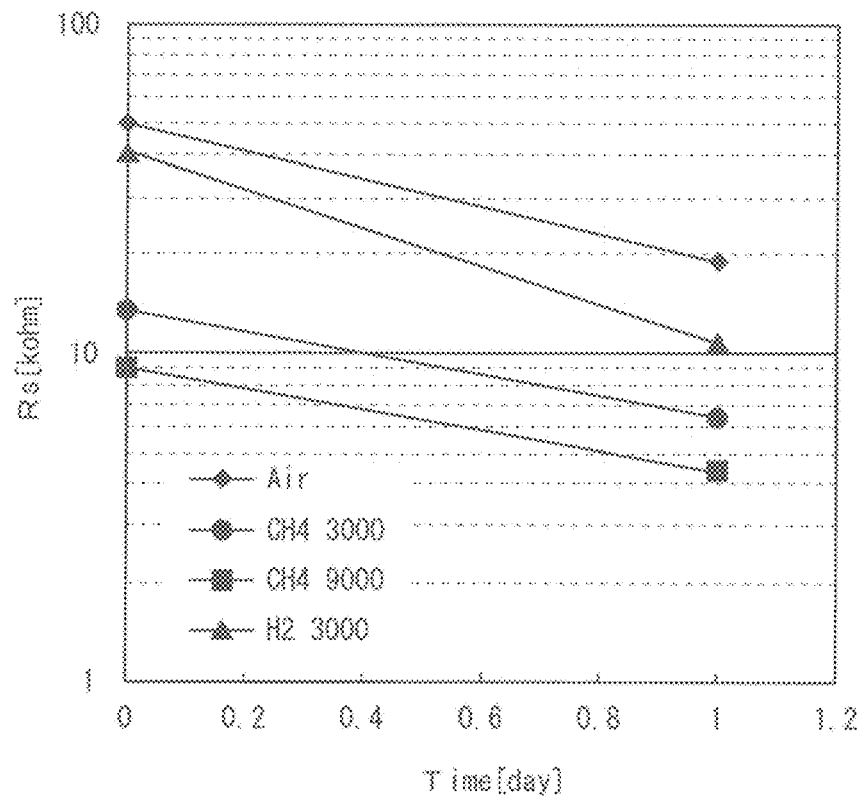
[FIG. 12] A diagram indicating behavior of resistance of another comparative gas sensor in air, in hydrogen, and in isobutane, during a durability test to siloxanes, with a mesoporous silica filter comprising rod-like particles.

FIGS. 10-12 indicate the influence of the sulfo group and Zr in the mesoporous silicas. Hydrogen and methane were detected, the temperature of the gas sensing element was 450° C. when the heater was on, and the poisoning condition was the same to those in FIGS. 8 and 9. FIG. 10 indicates the result of the mesoporous silica comprising plate-like particles and including the sulfo group (45 mg of 10SA-Zr-SBA-15-p, embodiment); FIG. 11 indicates the result of the plate-like mesoporous silica without the sulfo group (60 mg of SBA-15-p, comparative example); and FIG. 12 indicates the result of the rod-like mesoporous silica (75 mg of SBA-15, comparative example).

Plate-like 10SA-Zr-SBA-15-p including the sulfo group and Zr element afforded stable gas sensor characteristics for 20 days. SBA-15-p afforded stable gas sensor characteristics for 5 days, but rod-like SBA-15 caused poisoning in one day. The durability against the poisoning among the gas sensors was in the order of 10SA-Zr-SBA-15-p (Embodiment) >10SA-SBA-15-p>Zr-SBA-15-p>SBA-15-p>SBA-15.

The H+ content of the mesoporous silicas increased with the sulfo group content (FIG. 4). The atomic ratio of S and Si in the mesoporous silicas are, for example, 1:100-1:4 and preferably is 1:20-1:4. The above durability order corresponds to the capacity of ring-opening-polymerization of siloxanes by the sulfo group (FIG. 5) and to the increase in H+ acid content of the mesoporous silicas by Zr element (FIG. 4). More, the plate-like mesoporous silicas enhance more remarkably the anti-poisoning performance of the gas sensors than the rod-like mesoporous silicas do.

The Best Embodiment

For easily obtaining the filter material, silica-gel was used as the inorganic porous support, the filter material was prepared, and the gas sensor in FIG. 6 was assembled and was driven as shown in FIG. 7. The silica-gel support had 800 m2/g BET specific surface area, 1.24 cm3/g porous volume, and the porosity distribution from 3 to 20 nm measured from the saturation adsorption amount of nitrogen during the BET specific surface area measurement.

Metal compound aqueous solutions were impregnated as the starting materials of the Lewis acid in the support, was dried in air at 80° C. for 12 hours, and was baked at 300° C. for 12 hours so as to load the metal element as Lewis acid. For example, a zirconium oxychloride aqueous solution was used in the case of Zr. During the baking at 300° C., the zirconium oxychloride was decomposed, and Zr element is considered dispersing in the silica-gel as fine oxide clusters. In particular, since the thermal decomposition was performed for 12 hours at 300° C., zirconium element is estimated dispersing mainly as an oxide in the silica-gel. A Zr compound may be added to a precursor of silica-gel, such as silica-zol, and Zr may be solved in the silica-gel framework, with substituting for Si.

p-Toluene sulfonic acid was used as an organic sulfonic acid compound having sulfo group. Zirconium oxychloride was loaded to silica-gel and was baked at 300° C. Then, an aqueous solution of p-toluene sulfonic acid was impregnated in the silica-gel and was dried at 80° C. for 12 hours. Thus, p-toluene sulfonic acid was loaded to the silica-gel having Zr. The loading amount was 5 wt % p-toluene sulfonic acid per 100 wt % silica-gel support, and the S element concentration was 0.93 wt % in 100 wt % silica-gel support. Further, 5 wt % Zr in metal reduction was present in 100 wt % silica-gel support (55 mmol Zr/100 g SiO2).

With respect to the metal element concentrations as the Lewis acid ingredient in the silica-gel, the weights of the metal element per 100 wt % silica-gel support are shown in wt % unit, and, in the embodiment, the Zr concentration was, for example, 5 wt %. With respect to the organic sulfonic acid concentrations in the silica-gel, the organic sulfonic acid compound was, for example, 5 wt % per 100 wt % silica-gel support. A silica-gel including 5 wt % Zr element and 5 wt % p-toluene sulfonic acid is represented as Zr(5)/TSA(5)/SiO2. Regarding the organic sulfonic acid compound concentration, the S element concentration making sulfo group is preferably down to 0.2 g and up to 4 g in 100 g silica-gel support. The metal element concentration, such as Zr concentration for Lewis acid, is preferably down to 10 mmol and up to 200 mmol in 100 g silica-gel support. As a remark, some of p-toluene sulfonic acid is considered forming a Zr salt and the rest is considered not forming the Zr salt.

In place of p-toluene sulfonic acid, other sulfonic acids, such as phenol sulfonic acid, catechol di-sulfonic acid, bisphenol sulfonic acid, may be loaded in the silica-gel. The organic sulfonic acid compound may be loaded by supporting an organic S compound, such as a thiol, in the inorganic porous support, and then, by oxidizing it by hydrogen peroxide and so on.

Filter

With usage of the following filter materials, gas sensors shown in FIG. 6 were prepared:

SiO2 including 5 wt % Zr in metal reduction and 5 wt % p-toluene sulfonic acid (Specimen 1: Zr(5)/TSA(5)/SiO2 50 mg);

Simple SiO2 used in Specimen 1, without a sulfonic acid compound nor a Lewis acid (Specimen 2: SiO2 50 mg);

Silica-gel supporting zirconium sulfate (10 wt % zirconium sulfate: 100 w % silica-gel), prepared by loading aqueous zirconium sulfate solution in the silica-gel of Specimen 2 and drying at 80° C. for 12 hours (Specimen 3: 10 wt % Zr(SO4)2/SiO2 30 mg);

Silica-gel supporting zirconium sulfate (5 wt % zirconium sulfate: 100 w % silica-gel), prepared by loading aqueous zirconium sulfate solution in the silica-gel of Specimen 2 and drying at 80° C. for 12 hours (Specimen 4: 5 wt % Zr(SO4)2/SiO2 30 mg);

Silica-gel supporting 5 wt % zirconium element in metal reduction without S element, prepared from the silica-gel of Specimen 2 (Specimen 5: Zr(5)/SiO2 50 mg); and Plate-like mesoporous silica supporting 10 atomic % S and 5 atomic % Zr in the atomic ratio to Si (Specimen 6: 10SA-Zr-SBA-15p 40 mg).

Since both the durability against siloxanes and the detection delay determine the filter performance, the amounts of the specimens were determined such that the detection delay becomes uniform. In particular, the mounts of the filter materials were 50 mg for Specimens 1, 2, 5; 30 mg for Specimens 3, 4; and 40 mg for Specimens 6 (Specimen 6;

10SA-Zr-SBA-15p) so that the detection delays for isobutane detection were uniformly 25 seconds.

Figure 13:
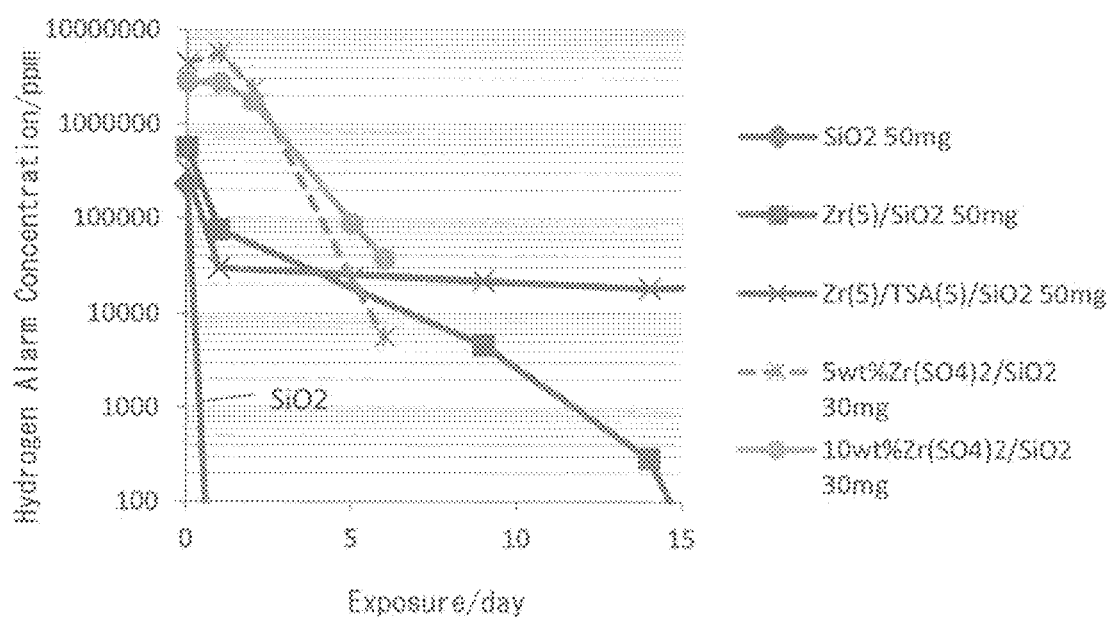
[FIG. 13] A diagram indicating behavior of resistance of a gas sensor according to the best embodiment in hydrogen during a durability test to siloxanes.
Figure 14:
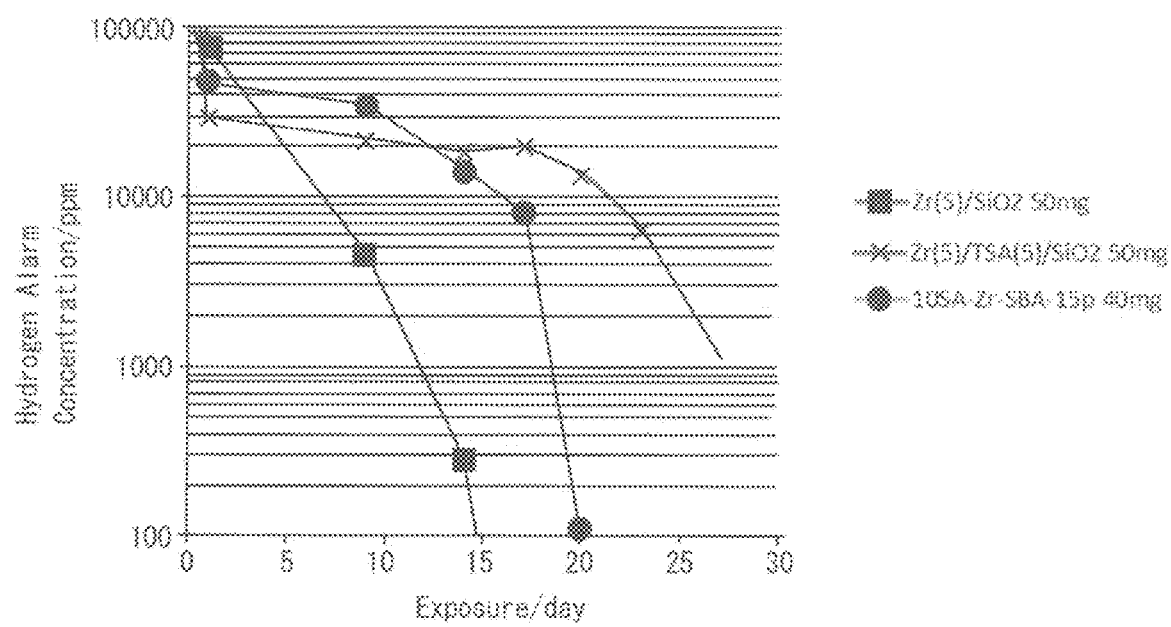
[FIG. 14] A diagram indicating behavior of resistances of the gas sensor according to the best embodiment and of a gas sensor according to the embodiment with the mesoporous silica in hydrogen during a durability test to siloxanes.

In an atmosphere containing each 30 ppm of M3, D4, and D5 siloxanes, the gas sensors were driven, and the behavior of hydrogen alarm concentrations were observed. FIG. 13 shows the results in silica-gel supports (Specimens 1-5) and FIG. 14 shows the comparison between silica-gel and mesoporous silica. Here, the hydrogen alarm concentration is the hydrogen concentration where the gas sensor resistance coincides with the initial resistance in 3000 ppm methane. Further, the siloxane concentration in the experiment is unrealistically high and can not occur in real environments.

High durability was exhibited, when Zr and p-toluene sulfonic acid were loaded in SiO2. In the SiO2 sequence in FIG. 13, the durability increased in the order of SiO2<10 wt % Zr(SO4)2/SiO2≈5 wt % Zr(SO4)2/SiO2<Zr(5)/SiO2<Zr(5)/TSA(5)/SiO2. Further, Specimen 3 (10 wt % Zr(SO4)2/SiO2) and Specimen 4 (5 wt % Zr(SO4)2/SiO2), both Zr sulfate being loaded in silica-gel, had lower durability than Specimen 5 (Zr(5)/SiO2). This indicates the decrease in siloxane adsorption activity or polymerization activity by the formation of a salt between Zr and sulfate ion.

As shown in FIG. 14, Specimen 1 (Zr(5)/TSA(5)/SiO2) had higher durability than Specimen 6, 10SA-Zr-SBA-15p, plate-like mesoporous silica supporting Zr and sulfonic acid.

Further Search for Inorganic Supports

Figure 15:
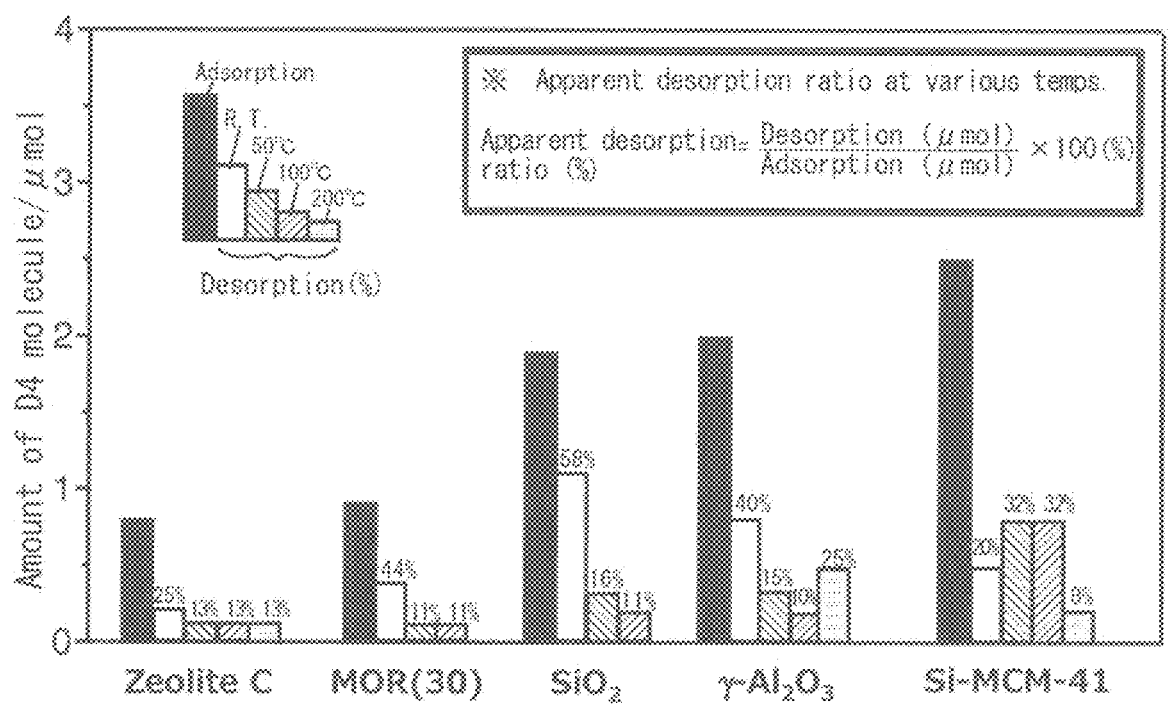
[FIG. 15] A diagram indicating the desorption amounts of siloxanes from various inorganic supports, from room temperature to 200° C.

Other supports than silica-gel and mesoporous silica were searched. As simple supports without Zr nor sulfo group, Zeolite C, MOR(30), fumed SiO2, γ-Al2O3, and Si-MCM-41 (mesoporous silica) were used; the specimens were 10 mg. The specimens were placed in a measurement cell, 0.5 Ton of D4 as siloxane was introduced twice, and by the pressure changes between before and after D4 adsorption, the adsorption amounts were measured. Then, the remaining D4 in the gas phase was removed, the desorption amount of D4 for 1 hour at room temperature and desorption amounts of D4 for every 20 minutes at 50° C., 100° C., and 200° C. were measured with usage of a liquid nitrogen trap. The results are shown in FIG. 15.

From MOR(30) and fumed SiO2, the desorption amounts at room temperature were large, and the desorption completed before 200° C. This indicates the weak interaction between these adsorbents and siloxane. Zeolite C andy-Al2O3 showed large desorption quantities at room temperature, while showed siloxane desorption at 200° C. This indicates the co-existence of strongly adsorbed siloxane and weakly adsorbed siloxane. Si-MCM-41 showed larger amounts of siloxane desorption at 50° C. and 100° C. than at room temperature; this indicates strong adsorption of siloxane.

Figure 16:
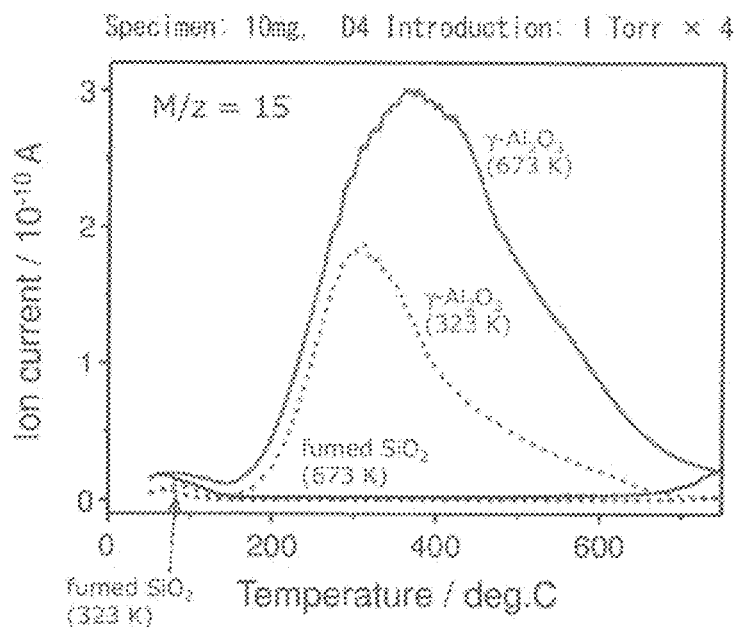
[FIG. 16] A diagram indicating thermal desorption spectra of a siloxane from γ-Al2O3 and fumed SiO2: numerals in parentheses indicate pretreatment temperatures; Lewis acid or organic sulfonic acid compounds are not loaded.

FIG. 16 shows the thermal desorption spectra of siloxane from fumed SiO2 and γ-Al2O3; the amount of the specimens was 10 mg, and the specimens were evacuated at 673K or 323K for removing adsorbed water. 1 Torr of D4 was introduced four times. In the fumed SiO2, the influence of the pretreatment temperature was small, and in γ-Al2O3, the adsorbed water remained after the pretreatment at 323K and the siloxane adsorption was made weaker.

Figure 17:
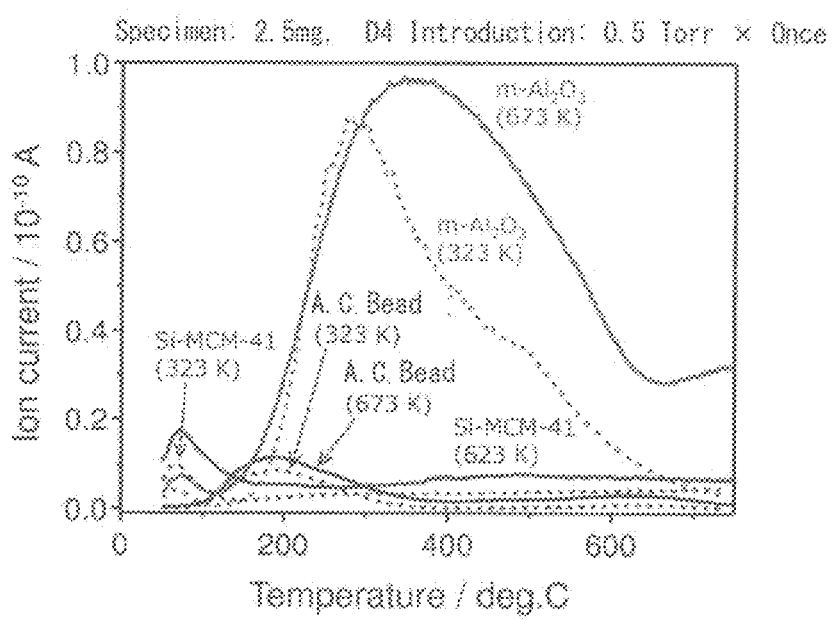
[FIG. 17] A diagram indicating thermal desorption spectra of a siloxane from m-Al2O3, mesoporous silica, and active charcoal: numerals in parentheses indicate pretreatment temperatures; Lewis acid or organic sulfonic acid compounds are not loaded.

FIG. 17 shows the thermal desorption spectra of siloxane from m-Al2O3, Si-MCM-41, and bead-like active charcoal, and the measurement condition was the same to those in FIG. 16. In Si-MCM-41 and bead-like active charcoal, the influence of the pretreatment temperature was small, but in m-Al2O3, the adsorbed water remained after the pretreatment at 323K and the siloxane adsorption was made weaker.

Figure 18:
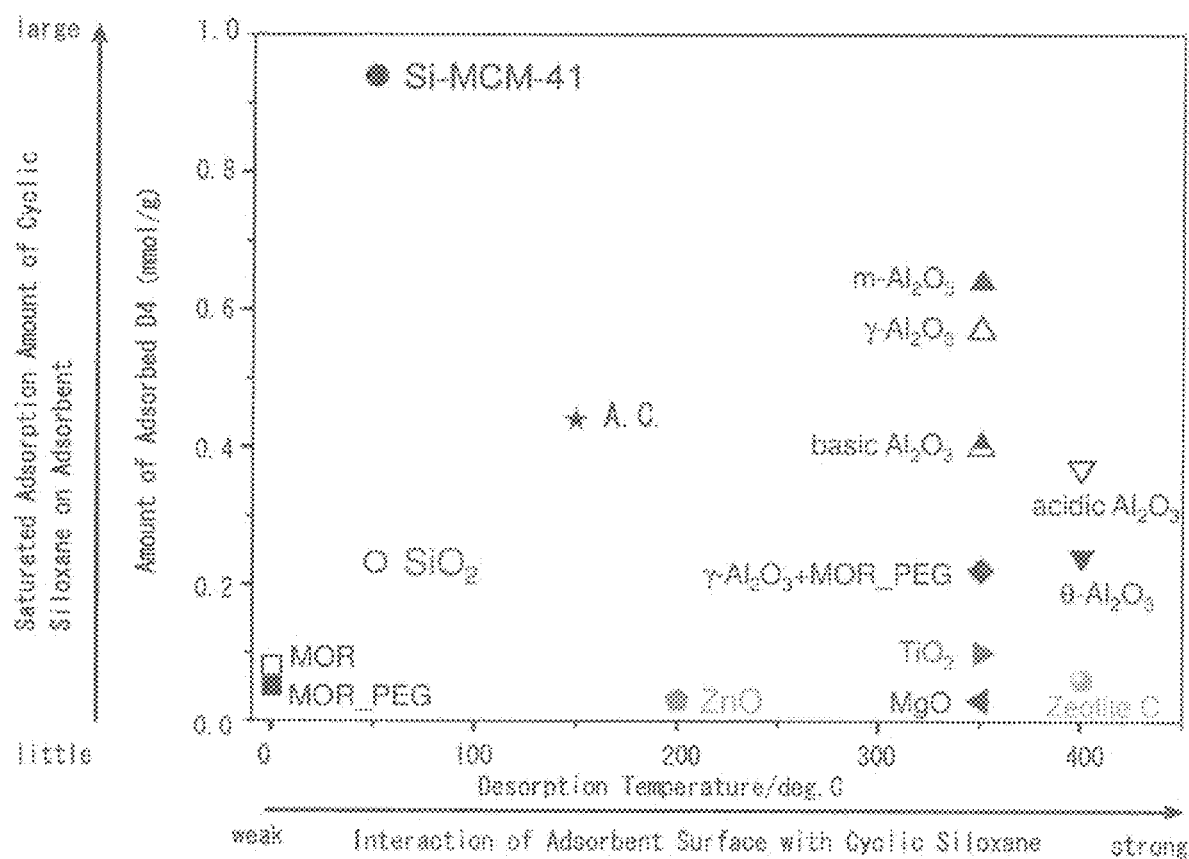
[FIG. 18] A diagram indicating saturated adsorption amounts and desorption temperatures of a siloxane in and from various inorganic supports: Lewis acid or organic sulfonic acid compounds are not loaded.

FIG. 18 shows the saturation adsorption amounts of D4 (at about 80% saturation pressure) and peak desorption temperatures of D4 for various inorganic porous supports. In alumina, such as m-Al2O3 and γ-alumina, the saturation adsorption amounts were large and the desorption temperatures were high. Therefore, alumina, such as γ, m, η, amorphous alumina, may be loaded with an organic sulfonic acid compound having sulfo group and a Lewis acid including Zr and so on, to prepare the filter. Further, as is shown in FIGS. 16, 17, the surface of alumina may be reformed by catechol or the like to make the water adsorption weaker.

DESCRIPTION OF CHARACTERS 2 gas sensor
4 gas sensing element
10 filter

What is claimed is:

1. A gas sensor comprising a gas sensing element and a filter arranged at a position nearer to atmospheres to be detected than the gas sensing element,
    wherein said filter comprises an inorganic porous support supporting both an organic sulfonic acid compound including sulfo group (—SO3H) and a Lewis acid consisting of zirconia.

2. The gas sensor according to claim 1, wherein said inorganic porous support includes at least a member selected from the group consisting of plate-like mesoporous silica, silica-gel other than mesoporous silica, or alumina.

3. The gas sensor according to claim 2, wherein said inorganic porous support includes the silica-gel other than mesoporous silica.

4. The gas sensor according to claim 1, wherein said filter is obtainable by fixing said zirconia in the inorganic porous support and then, loading said organic sulfonic acid compound in the inorganic porous support.

5. The gas sensor according to claim 1, wherein said zirconia is solved in said inorganic porous support as a solid solution.

6. A method for producing a gas sensor comprising a gas sensing element and a filter arranged at a position nearer to atmospheres to be detected than the gas sensing element, comprising:
    a step for loading, in an inorganic porous support, at least a salt of Zr element, and then, thermally decomposing said salt to load an Lewis acid consisting of zirconia; and
    a subsequent step for loading, in said inorganic porous support, an organic sulfonic acid compound including sulfo group (—SO3H) to prepare a material of said filter.

* * * * *